United States Patent
Waynick (10) Patent No.: US 6,599,337 B2
(45) Date of Patent: Jul. 29, 2003

(54) SELECTION OF MATERIALS TO TEST FOR AND/OR REMOVE DRAG REDUCER ADDITIVE IN LIQUID HYDROCARBON FUELS

(75) Inventor: John Andrew Waynick, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 0 days.

(21) Appl. No.: 10/124,974

(22) Filed: Apr. 18, 2002

(65) Prior Publication Data

US 2003/0019149 A1 Jan. 30, 2003

Related U.S. Application Data

(60) Provisional application No. 60/284,634, filed on Apr. 18, 2001.

(51) Int. Cl.[7] .............. C10L 1/14; C10L 1/12; G01N 33/26
(52) U.S. Cl. .............. 44/903; 44/457; 436/60; 210/728
(58) Field of Search .............. 44/457, 903; 436/60; 210/728

(56) References Cited

U.S. PATENT DOCUMENTS

| | | |
|---|---|---|
| 1,198,039 A | 9/1916 | Krause |
| 2,546,903 A | 3/1951 | Morrell |
| 2,744,938 A | 5/1956 | Urban, Jr. |
| 2,762,852 A | 9/1956 | Litton |
| 3,366,582 A | 1/1968 | Adams et al. |
| 3,977,969 A | 8/1976 | Zall |
| 4,451,377 A | 5/1984 | Luxemburg |
| 4,502,957 A | 3/1985 | Jehle et al. |
| 4,508,851 A | 4/1985 | Izumi et al. |
| 4,599,117 A | 7/1986 | Luxemburg |
| 4,758,354 A | 7/1988 | O'Mara et al. |
| 5,225,081 A | 7/1993 | Brownawell |
| 5,736,053 A | 4/1998 | Ikushima et al. |
| 5,788,865 A | 8/1998 | Smirnov et al. |
| 5,833,862 A | 11/1998 | Holland |
| 5,884,777 A | 3/1999 | Pan et al. |
| 5,888,402 A | 3/1999 | Hommeltoft et al. |
| 5,891,324 A | 4/1999 | Ohtsuka |
| 5,893,398 A | 4/1999 | Garrett, Jr. |
| 5,900,153 A | 5/1999 | Sanford |
| 6,024,880 A | 2/2000 | Ciora, Jr. et al. |
| 6,027,653 A | 2/2000 | Holland |
| 6,042,722 A | 3/2000 | Lenz |
| 6,056,805 A | 5/2000 | Litwin et al. |
| 6,082,392 A | 7/2000 | Watkins, Jr. |
| 6,103,127 A | 8/2000 | Pourfarzaneh |

*Primary Examiner*—Cephia D. Toomer
(74) *Attorney, Agent, or Firm*—Paula D. Morris & Associates, P.C.

(57) ABSTRACT

A method for selecting an effective removal agent and a method of removing drag reducer additive from liquid hydrocarbon fuels, preferably gasoline or jet fuel.

103 Claims, 3 Drawing Sheets

SELECTION OF MATERIALS TO TEST FOR AND/OR REMOVE DRAG REDUCER ADDITIVE IN LIQUID HYDROCARBON FUELS

CROSS REFERENCE TO RELATED APPLICATIONS

The present application claims the benefit of Provisional Application Ser. No. 60/284,634, filed Apr. 18, 2001.

FIELD OF THE INVENTION

The invention relates to the selection of "drag reducer additive" removal agents, and to the detection and/or removal of "drag reducer additive" (DRA) from liquid hydrocarbon fuels.

BACKGROUND

In order to move fluid through pipelines, into or out of wells, or through equipment, energy must be applied to the fluid. The energy moves the fluid, but is lost in the form of friction. This frictional pressure drop, or drag, restricts the fluid flow, limiting throughput and requiring greater amounts of energy for pumping.

Materials can be added to flowing fluids in order to reduce the energy lost due to friction, or drag, thus permitting the movement of more fluid at the same differential pressure. The resulting reduction in frictional pressure drop improves pumping efficiency, lowers energy costs, and increases profitability. Materials for reducing drag in flowing fluids are generally known by the generic names "flow improver" or "drag reducer additive" (sometimes referred to as "DRA").

Unfortunately, whether in the virgin form or in the sheared or partially sheared form, and despite the fact that it is intentionally added to certain fuels, drag reducer additive nonetheless is a "contaminant" in liquid hydrocarbon fuels, and has the potential to cause a number of problems. For example, the presence of drag reducer additive in motor gasoline, even in the sheared form, has caused increased intake valve deposits, plugging of fuel filters, and increased combustion chamber deposits. In diesel fuels, drag reducer additive may cause plugging of fuel filters and strainers and increased fuel injector deposits. Drag reducer additive is prohibited in aviation turbine fuels, although it has been observed as a contaminant due to accidental addition or other non-intentional means. The presence of drag reducer additive in aviation turbine fuel may result in downgrading of the entire batch to non-aviation kerosene or diesel fuel, both of which generally have less market value.

Viable methods of detecting and quantifying drag reducer additive in liquid hydrocarbon fuels commonly employ gel permeation chromatography, which is time consuming and expensive. Because of this, contaminated liquid hydrocarbon fuels often are used, despite the potential problems if drag reducer additive is present. Contaminated aviation turbine fuels may be diverted to other uses or returned to a refinery for reprocessing, either of which results in additional expense. Methods are needed to easily and inexpensively select materials that are capable of testing for the presence of drag reducer additive and/or capable of removing drag reducer additive from liquid hydrocarbon fuels.

BRIEF SUMMARY

Methods are provided for selecting one or more effective removal agents and using said agents to substantially reduce the concentration of drag reducer additive in a liquid hydrocarbon fuel.

DETAILED DESCRIPTION

The application provides a method for inexpensively and effectively selecting removal agents for drag reducer additive from liquid hydrocarbon fuels, preferably motor gasoline or jet fuel, most preferably motor gasoline. The invention also provides methods of using the selected removal agents to test for the presence of drag reducer additive, and to reduce the concentration of drag reducer additive in "contaminated" hydrocarbon fuel. As used herein, the word "contaminated" refers to DRA which is found in the fuel due to either intentional addition or unintentional addition.

"Liquid Hydrocarbon Fuel"

By "liquid hydrocarbon fuel" is meant any hydrocarbon that is liquid under conditions of transport and/or storage. Suitable liquid hydrocarbon fuels include, but are not necessarily limited to those having a boiling range of from about 150° F. to about 750° F. which may be used as a fuel. In one embodiment, the liquid hydrocarbon fuel is selected from the group consisting of liquefied natural gas (LNG), liquefied petroleum gas (LPG), motor gasoline, aviation gasoline, diesel fuel, home heating oil, kerosene, jet fuel, No. 2 oil, residual fuel, No. 6 fuel, or bunker fuel. In a preferred embodiment, the liquid hydrocarbon fuel is selected from the group consisting of diesel fuel, jet fuel, aviation gasoline, and motor gasoline. In a more preferred embodiment, the liquid hydrocarbon fuel is selected from the group consisting of jet fuel and motor gasoline. Motor gasoline is a preferred embodiment, at least in part due to commercial potential. Jet fuel is a preferred embodiment, at least in part due to the stringent requirements applicable to jet fuel and drag reducer additive.

The Selection Agent and Removal Agent

Without limiting the invention to a particular mechanism of action, suitable "selection agents," and/or "removal agents" (hereinafter collectively referred to as "agents") are believed to be porous materials comprising pores having a hydrophobic/hydrophilic property that is compatible with or provides a chemical attraction to pendant groups of the drag reducer additive for which testing is to be conducted. Suitable agents include, but are not necessarily limited to carbonaceous materials, which may be in the form of crushed particles or granules, powder, cylinders, globules, fibers, or honeycombs. Preferred agents are in the form of particles or granules. A more preferred agent is activated carbon in powder or granule form. The agents, preferably activated carbon, have a porosity sufficient to provide an adsorption capacity of about 0.05 wt. % or more, preferably about 0.2 wt. % or more.

Activated carbon is produced from a large variety of substances, such as coal, bagasse, corn cobs, other farm products, cereals, blood, kelp, petroleum sludges, petroleum residue, coconuts, nutshells, various woods, fruit pits, and many other sources. Carbon is activated by methods well known in the art, such as high temperature and contact with water vapor or carbon dioxide, or acid treatment with zinc chloride, phosphoric acid, concentrated sulfuric acid, and the like. Suitable candidate activated carbons are commercially available, for example, from Allchem Industries, Inc., Beta Chemicals, Calgon, Coyne Chemical Co., Elf Atochem North America, Inc. (Performance Products), R. W. Greef & Co, Inc., Kingshine Chemical Co., Ltd., Mays Chemical Co., Inc., Norit Americas, Inc., U.S. Filter, Superior Graphite, Asbury Graphite Mills, Inc., Mitsubishi International Corp. (Industrial Specialty Chemicals Div.), Spectrum Chemical Mfg. Corp., and others.

The present invention is based on the surprising finding that certain carbonaceous materials are effective to bind and remove drag reducer additive, preferably polyolefin polymers, from liquid hydrocarbon fuels. This result is unexpected because polyolefin polymers are extremely non-polar in nature. Carbonaceous materials typically are used to selectively adsorb or remove polar materials from various substrates. The polyolefin polymer is physically or chemically bound to the carbonaceous material in a manner which, although not limited to a single mechanism, is herein called "adsorption." In a preferred embodiment, the binding is irreversible—at least under the conditions of testing, detecting, and/or removing of DRA from liquid hydrocarbon fuel, as described in more detail below.

Without limiting the invention to a particular theory or mechanism of operation, suitable removal agents are believed to comprise ducts or pores having a hydrophobic/hydrophilic property that provides a chemical attraction to pendant groups on the drag reducer additive. The chemical attraction is believed to bring the pendant groups on the drag reducer additive into proximity and orientation with the pore surface of the agent, thereby immobilizing the pendant groups. Because many pendant groups on a given drag reducer molecule are simultaneously immobilized, the drag reducer molecule is strongly immobilized, "Drag Reducer Additive"

The term "drag reducer additive" (i.e. DRA) is defined to mean polyolefin polymers comprising polyolefin moieties which are introduced into petroleum liquids for the purpose of reducing fluid flow drag. The drag reducer additive may comprise other components besides the polyolefin moieties. Examples of such components include, but are not necessarily limited to surfactant, catalyst residue, other additives, and other byproducts from the production of the polymer. The polymer itself may contain other non-olefin monomer units as well. In a preferred embodiment, the drag reducer additive includes, but is not necessarily limited to, non polar long-chain polyolefin polymers having a "peak" molecular weight sufficiently high to allow the polymers to reduce fluid flow drag. Suitable polymers are believed to have a molecular weight of about 1 million Daltons or more, more preferably about 10 million Daltons or more, most preferably about 25 million Daltons or more. The "peak" molecular weight refers to the peak that typically is measured as the drag reducer is eluted and detected during gel permeation chromatography. Commercially available drag reducer additives include, but are not limited to, CDR® Flow Improver and LiquidPower™, manufactured by Conoco Specialty Products, Inc., EN-660 Flow Improver, manufactured by Energy 2000 LLC, and FloXS and FloXL, manufactured by Baker Petrolite.

The exact mechanism by which a drag reducer additive reduces drag in flowing liquid hydrocarbons is not completely known. However, a drag reducer additive apparently alters the turbulent flow regime of the liquid hydrocarbons. In a pipeline, this flow regime is comprised of at least three regions. At the center of the pipe is a turbulent core, which is the largest region and includes most of the fluid in the pipe. This is the zone of eddy currents and random motions for which turbulent flow is named. Nearest to the pipe line wall is the laminar sublayer. In this zone, the fluid moves laterally in "sheets". Between the laminar layer and the turbulent core lies the "buffer zone". It appears that much of the turbulence which exists in turbulent flow develops when a portion of the laminar sublayer, called a "streak", moves up to the buffer zone, where it begins to vortex and oscillate, finally breaking up and throwing fluid into the core. This ejection of fluid into the core is called a "burst". The burst creates the turbulence in the core, and energy is wasted in different directions. Drag reducer additive appears to interfere with the bursting process and prevent or reduce the degree of turbulence by stretching in the flow, absorbing the energy in the streak, and thereby preventing bursts.

As liquids containing drag reducer additive travel through pumps, pipelines and other equipment, the drag reducer additive typically degrades through shearing action, resulting in a reduction in the molecular weight of the drag reducer additive. The degraded drag reducer additive is known as sheared or partially sheared drag reducer additive. Upon reaching the ultimate destination, liquid hydrocarbon fuels which have been shipped using drag reducer additive may contain a significant amount of drag reducer additive, including that in the sheared and partially sheared form.

Method for Selecting Effective Removal Agents

Certain carbonaceous materials are more effective than others as selection agents, detection agents, and/or removal agents for a given drag reducer additive. A "quick test," defined to mean the procedure described below, may be used to screen candidate removal agents.

In a "quick test," the candidate selection agent, preferably a finely powdered carbonaceous material, most preferably a finely powdered activated carbon, is mixed with a sample of motor gasoline. The size of the sample of motor gasoline, the quantity of the drag reducer additive, and the quantity of activated carbon may vary. In a preferred embodiment, about 100 ml of motor gasoline comprising from about 0.5 ppm to about 1,000 ppm, preferably about 20 ppm, of a selected drag reducer additive is stirred, preferably with a magnetic stirring bar, to create a moderate vortex. From about 0.1 to about 2 grams, preferably about 0.5 grams, of the candidate selection agent quickly is placed in the agitating motor gasoline.

The agitating mixture is observed to determine whether (a) the mixture forms a substantially uniform dispersion of the candidate selection agent in the fluid (which, in the case of activated carbon, gives the appearance of a "black blizzard" or black "tornado"), or (b) the candidate selection agent takes on a somewhat shiny or glossy appearance, and forms agglomerates or "clumps" that either settle to the bottom or spin with the agitation of the mixture. The agglomerates or "clumps" form relatively quickly, for example, within about 30 seconds, preferably within about 10 seconds after addition to the agitated mixture. Candidate selection agents that meet criterion (b) are "effective selection agents," which also are useful as "detection agents" for the presence of drag reducer additive in the sample fuel. Candidate selection agents that meet criterion (b) are likely to be "effective removal agents" from gasoline, and are expected to be effective removal agents from other hydrocarbon fuels.

The agglomeration or clumping of the carbonaceous materials during the above described "quick test" falls into one of three rheological behavior categories (RBC), sometimes referred to herein as having an "RBC of 1," an "RBC of 2," or an "RBC of 3." As used herein, these terms are defined to mean the following:

RBC of 1: Discrete clumps exist throughout the entire stirring process wherein little or no finely divided carbonaceous material exists and the DRA/fuel mixture remains mostly clear, except for the small clumps of carbonaceous material that swirl around in a vortex. When the stirring stops, small clumps immediately settle to the bottom, typically within about 10 seconds or less, leaving a clear supernatant solution;

RBC of 2: Discrete clumps form but then break up and disperse. Remaining clumps are very small, giving the impression that the carbonaceous material has uniformly dispersed throughout the DRA/fuel mixture; however, when the stirring stops, the carbonaceous material settles very quickly, typically within about 10 seconds or less, leaving a clear supernatant solution. The carbon particles may be fine enough to appear as a powder;

RBC of 3: Little or no initial clumping is observed. The carbonaceous material disperses uniformly throughout the DRA/fuel mixture. The carbonaceous material does not rapidly settle, but requires up to several minutes to settle. The supernatant is not clear, holding carbonaceous material in suspension.

All activated carbons remove drag reducer additive from liquid hydrocarbon fuels, preferably gasoline or jet fuel, to some extent, and all activated carbons are suitable for use according to the methods described herein. Suitable activated carbons include those having an RBC of 1, 2, or 3. However, preferred, more efficient activated carbons for use according to the methods described herein have an RBC of 1 or 2, more preferably an RBC of 1.

In order to assess precisely which selection agent is most effective to remove a given DRA from a given substrate, the percent polymer removal is measured by gel permeation chromatography (GPC). The mixture preferably is filtered through a filter of a porosity sufficient to remove all activated carbon from the resulting filtrate. A preferred period of time for stirring before filtering is 10 seconds or more, preferably 1 minute or more, more preferably 2 minutes or more, to insure that adsorption equilibrium has been attained. If kinetic information regarding the adsorption of DRA by the detection agent is desired, stirring times less than that required for complete adsorption can be used. Once filtered, the DRA/fuel mixture is analyzed, preferably by GPC. The GPC analysis of a DRA/fuel mixture that was treated with a given detection agent is compared to the GPC analysis of the same DRA/fuel mixture without treatment by the given detection agent. If this test is performed, then the detection agent(s) that remove the most DRA are selected as removal agents. Such procedures and the information therein gained is within the scope of this invention and use of such procedural modifications is well within that easily understood by those skilled in the art.

In the "quick test," described above, which uses 100 ml. fuel, 20 ppm polymer, and 0.5 gm of activated carbon, and conditions effective to provide intimate contact between the selection agent and the substrate, effective removal agents preferably reduce DRA concentration in the substrate, as measured by GPC, by about 3% or more, preferably by about 20% or more, more preferably by about 50% or more.

Detection of Drag Reducer Additive in a Given Substrate

Once effective agents for a given type of drag reducer additive in a given type of substrate have been identified, those candidates may be used as "detection agents," or as agents adapted to detect the presence of a given drag reducer additive in a sample of contaminated hydrocarbon fuel, preferably a contaminated motor gasoline or a contaminated jet fuel, most preferably a contaminated motor gasoline.

In order to test for or detect the presence of a given drag reducer additive in a sample, about 100 ml. of a candidate liquid hydrocarbon fuel, preferably motor gasoline, is stirred, preferably with a magnetic stirring bar, to create a moderate vortex. From about 0.1 to about 2 grams, preferably about 0.5 grams, of a chosen detection agent quickly is placed in the agitating motor gasoline. The agitated mixture is observed to determine whether (a) the mixture forms a substantially uniform dispersion of the candidate detection agent in the fluid (which, in the case of activated carbon, gives the appearance of a "black blizzard" or black "tornado"), or (b) the candidate detection agent takes on a somewhat shiny or glossy appearance, and forms agglomerates or "clumps" within about 30 seconds that either settle to the bottom or spin with the agitation of the mixture. The formation of agglomerates or clumps is an indication that DRA is present in the candidate motor gasoline.

Removal of Drag Reducer Additive From Liquid Hydrocarbon Fuels

It may be desirable simply to subject all of a given fuel at a given storage or transport site to a DRA removal procedure. Or it may be desirable to test for the presence of DRA before incurring the expense of removal.

Once preferred removal agents have been identified, the removal agent may be used to detect the presence of drag reducer additive from a given liquid hydrocarbon fuel, preferably motor gasoline or jet fuel, most preferably motor gasoline. Alternately, a given sample of hydrocarbon fuel is analyzed for DRA by gel permeation chromatography (GPC).

Preferably, GPC standards are prepared using DRA/fuel mixtures having 0 ppm DRA and mixtures having quantities of DRA above and below that encountered in the field. For example, the standards might contain 2 ppm DRA; 5 ppm DRA; 10 ppm DRA; 20 ppm DRA; 50 ppm DRA. The fuel or DRA/fuel mixture is prepared for injection onto the GPC column by first blowing the mixture down to incipient dryness with a gentle stream of warm air while maintaining the sample temperature sufficient to evaporate the bulk of the fuel, typically about at about 115° C. or higher. The residue is then re-dissolved in tetrahydrofuran (THF) so that the volumetric concentration factor is from about 2 to about 20, preferably about 10. The re-dissolved sample is then injected onto the GPC column and the sample is eluted with THF. Any DRA peak detected in a candidate sample is quantified by comparison with the standard solutions of DRA in THF that have been similarly prepared and analyzed. Other details of this GPC procedure including the column type, elution rate, detector equipment, etc. will be apparent to those skilled in the art of gel permeation chromatography.

When it is desired to remove DRA from a given fuel, one or more of effective removal agent(s) are incorporated into a system for filtering the DRA/fuel mixture and for removing drag reducer additive from that mixture. The filter may be in any suitable form and may be installed in a variety of locations. Suitable locations include, but are not necessarily limited to a pipeline to a fuel terminal, a delivery system between a fuel terminal and a tanker truck, a delivery system between two different tanker trucks, a delivery system from a tanker truck to a storage tank or to an engine, and, actually as a component of the engine, itself. In a preferred embodiment, the filter comprises a component of a fuel delivery system from a tanker truck to a jet engine. The filter may be used in substantially any type of delivery system. In each method, the carbonaceous material may be heated prior to being added to the DRA/fuel mixture. Heating removes any water adsorbed on the carbonaceous material.

Due to the difficultly in providing for incremental addition and agitation in most commercial situations, it may be preferred to simply pass the liquid hydrocarbon fuel through a bed of the removal agent until the removal agent must be replaced. In a preferred embodiment, the filtering system provides for agitation of the DRA/fuel mixture as incremental additions of a given removal agent are added to the DRA/fuel mixture. This procedure is sometimes herein referred to as the "stirring method" and/or the "shaking method." Where the substrate is gasoline, a preferred method of agitation is shaking. Where the substrate is a more viscous hydrocarbon fuel, such as jet fuel, a preferred method of agitation is stirring. In a preferred embodiment, a fixed amount of the effective removal agent(s) is added in increments of from about 1% to about 20% of the total amount to a given volume of DRA/fuel mixture, preferably while the mixture is agitated. At least in the case of less viscous liquid hydrocarbon fuels, such as gasoline, shaking provides the most intimate contact between the surface of the carbonaceous material and the DRA polymer in the DRA/fuel mixture and is a preferred method of agitation. Using incremental addition and shaking to remove DRA from gasoline, the percent polymer removal for a removal agent with an RBC of 1 often is greater than the percent polymer removal for a removal agent with an RBC of 2. Likewise, the percent polymer removal for a removal agent with an RBC of 2 often is greater than the percent polymer removal of a removal agent with an RBC of 3. The following is an example of how the system would be incorporated into a known fuel delivery system.

Civilian aircraft generally are serviced in hangers at airports. Military aircraft are serviced on the flight line, where a row of aircraft are parked away from a maintenance terminal and nearer to the runway, to be ready for mobilization. The distance from the flight line to the maintenance terminals may be as much as one mile. Servicing of aircraft, particularly military aircraft, typically is performed by shuttling service vehicles out to the flight line from the maintenance terminal where they perform the requisite service. Periodically, the servicing vehicles return to the maintenance terminal to themselves be refueled or for other servicing.

Figure 1:
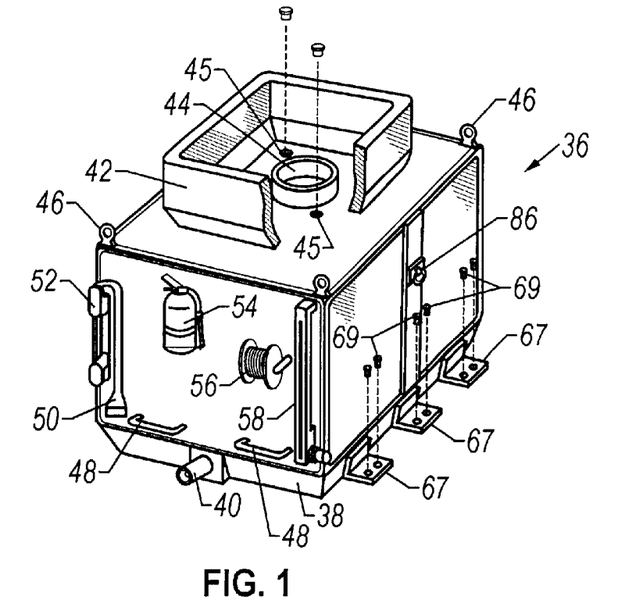
FIG. 1 depicts the tank of a refueling truck suitable for incorporating a filtering system using the principles described herein.

FIG. 1 illustrates a typical configuration for a tank 36 of a refueling truck. Each tank 36 is made of a material that is reasonably rigid and resistant to attack by the fluid it is designed to contain. Steel or polyethylene are suitable materials. Each tank has a tapered bottom 38 to facilitate drainage of its contents through a drain 40 and a funnel-shaped top 42 to catch spills when it is being filled at its inlet post 44. Air vents 45 allow air to escape from the tank 36 when it is being filled and allow air to enter the tank 36 when it is being drained. Each tank 36 has a hose 50 and a bracket 52 for storing the hose 50.

Figure 1A:
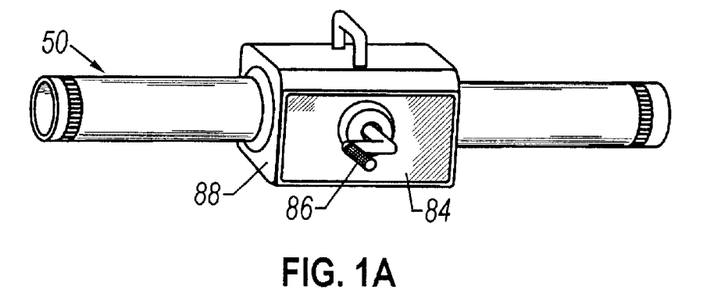
FIGS. 1A and 1B describe the hose of the tank in FIG. 1 in more detail.
Figure 1B:
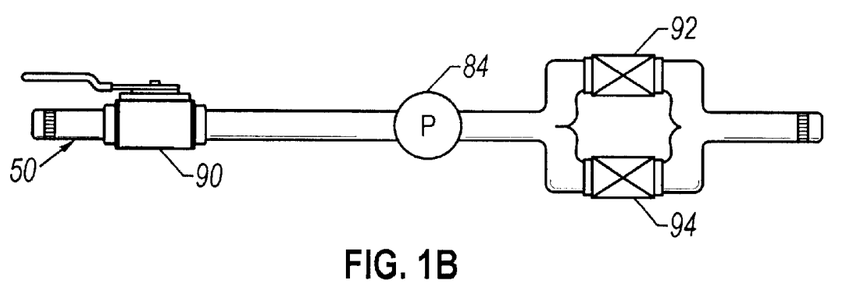

The transfer hose 50 is shown in more detail in FIGS. 1A and 1B, in perspective in FIG. 1A and in a schematic view in 1B. The transfer hose 50 has a manual pump 84 to start the flow of fluid, The manual pump 84 is operated by turning a handle 86 clockwise for fluid flow in one direction and counter-clockwise for fluid flow in the opposite direction. The pump is inside a housing 88 that contains several other components as illustrated in FIG. 1B, namely, a shutoff valve 90 and two one-way filters 92 and 94 to assure that the flow of fluid goes in the direction desired and dirt and debris are filtered out. A filter device 96 according to the present application is inserted either in series or in parallel with these one-way filters 92 and 94. Preferably, a filter device 96, such as a canister or other vessel containing the removal agent(s), is placed downstream of the filters 92 and 94 in order to improve efficiency and longevity of the operation. Most preferably, the canister or the other vessel is equipped with a system effective to provide incremental addition of the removal agent with agitation, preferably stirring. Typically, a tow truck pulls a trailer comprising the tank 36, and generally two other tanks, from the maintenance terminal to the flight line after the tank 36 and the other two tanks have been filled with diesel fuel, oil and jet fuel. At the flight line, the tow truck takes the trailer from one service vehicle of the first set to the next, adding small quantities to each of them or most of them, preferably just topping up their levels of fuel and oil until the tanks are empty.

One end of the transfer hose 50 is connected to the drain 40 and the other end put into the inlet tank of the vehicle being refueled. The shutoff valve 60 of the tank 36 is opened, and then the hose valve 90 is opened. The manual pump 84 is operated to cause fluid to flow from the tank 36 until the vehicle tank is approximately one-fourth full. The shutoff valve 6 is then closed, but the manual pump 8 continues to be operated until the fluid stops. Then hose shutoff valve 9 is closed. The hose 50 can then be disconnected and placed in the catch basin 64.

The invention will be better understood with reference to the following examples, which are illustrative only:

EXAMPLE 1

About 100 ml of motor gasoline comprising about 20 ppm of a selected drag reducer additive was stirred with a magnetic stir bar, to create a moderate vortex. A removal agent in the amount of 0.5 g was heated for approximately 1 hour at 125° C. to remove any water that may have been adsorbed by the removal agent. Once the removal agent had cooled, increments of about 0.02 to about 0.1 gram of the removal agent were placed in the agitating DRA/gasoline mixture, while stirring, until a total of about 0.5 gram had been added. The stirring was continued for approximately two to three minutes. The sample was allowed to settle for about 5 minutes.

EXAMPLE 2

About 100 ml of motor gasoline comprising about 20 ppm of a selected drag reducer additive was added to an 8 oz. bottle. A removal agent in the amount of 0.5 g was heated for approximately 1 hour at 125° C. Once the removal agent had cooled, an amount from about 0.02 to about 0.1 gram of removal agent was placed in the 8 oz. bottle containing the 100 ml DRA/gasoline mixture. The bottle was capped and vigorously shaken. This step was repeated until 0.50 g of the removal agent had been added to the DRA/gasoline mixture. The sample was then allowed to settle for about 5 minutes.

Figure 2:
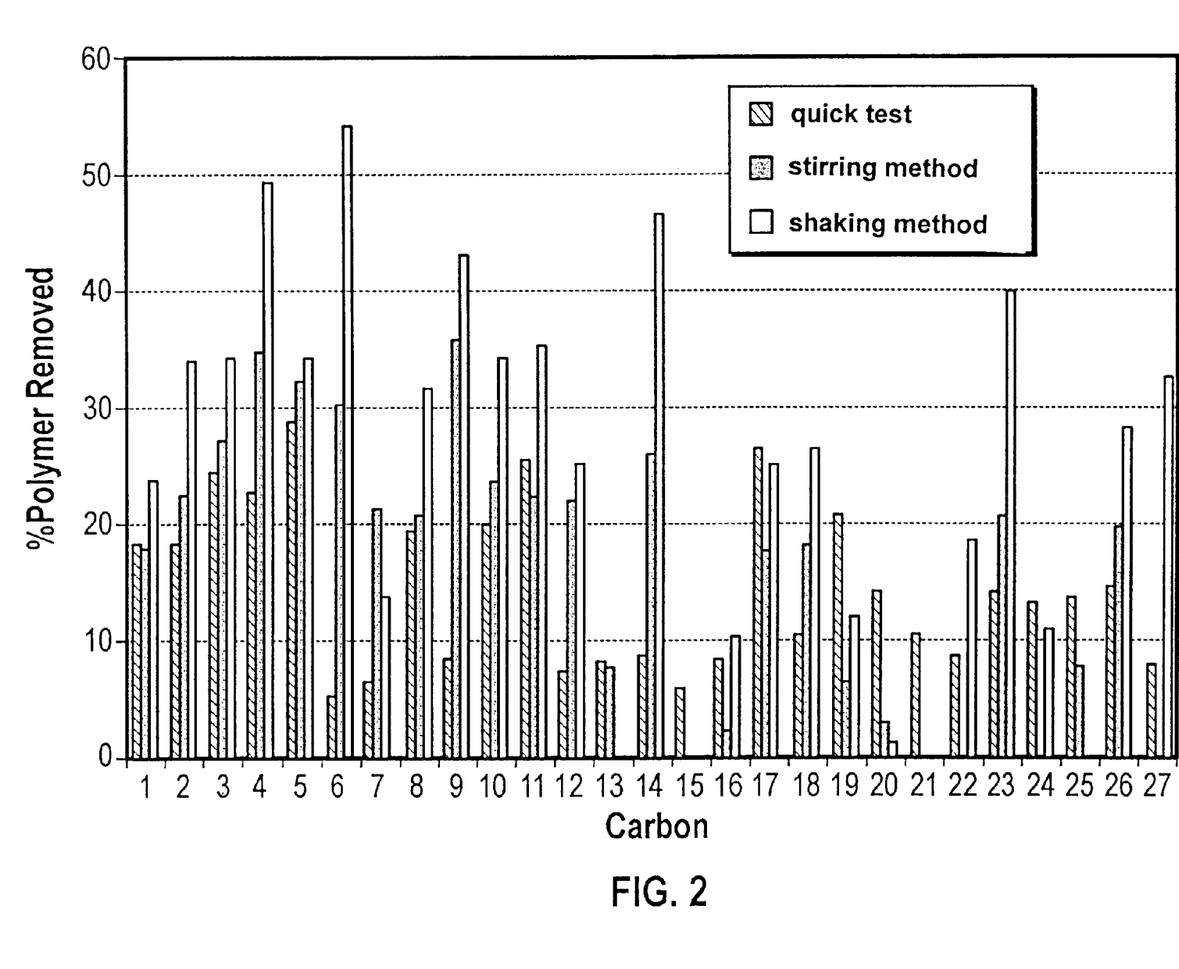
FIG. 2 depicts the percentage of polymer removal of candidate removal agents in Example 2.

The polymer adsorption of removal agents increased using the method of Example 2. Table 1 summarizes the % DRA polymer adsorbed for the quick test, and the stirring and shaking methods. In 18 of 27 removal agents tested, polymer removal effectiveness increased using the shaking method over the quick test. The highest removal effectiveness of the 27 removal agents tested was 53.9%, which corresponds to a polymer adsorption capacity of 0.18% (wt). FIG. 2 shows the performance of the removal agents in the quick test vs. the stirring method vs. the shaking method.

The removal agents listed in Table 1 are derived from numerous sources, including wood, coconut and other shells, peat, bituminous coal, lignite coal, and anthracite coal. Each carbon source material differs in surface area, pore size, density, and strength characteristics.

TABLE 1

| Sample with Source Material | % Polymer Removal Quick Test No Heat | % Polymer Removal Quick Test Heat | % Polymer Removal Shaking Method | % Polymer Removal Stirring Method | Delta | Max Delta | Carbon RBC (no heat) |
|---|---|---|---|---|---|---|---|
| Darco G-60 -peat | 11.4 | 18.1 | 23.7 | 17.7 | −0.4 | 5.6 | 2 |
| Calgon ADP -bituminous coal | 14.6 | 18.1 | 34.0 | 22.4 | 4.3 | 15.9 | 2 |
| Darco FGD -lignite coal | 23.3 | 24.5 | 34.2 | 27.1 | 2.6 | 9.7 | 2 |
| Norit SX Plus -peat | 27.9 | 22.7 | 49.3 | 34.7 | 12.0 | 26.6 | 1 |
| Filtercarb SX0 -coconut shell | 17.4 | 28.8 | 22.4 | 32.2 | 3.4 | −6.4 | 3 |
| Calgon RB -bituminous coal | 10.4 | 5.1 | 53.9 | 30.1 | 25.0 | 48.8 | 1 |
| Calgon APL -bituminous coal | 0.00 | 6.5 | 13.6 | 21.2 | 14.7 | 7.1 | 1 |
| Norit HDB -lignite coal | 24.8 | 19.4 | 31.5 | 20.7 | 1.3 | 12.1 | 2 |
| Norit A Supra -peat | 29.2 | 8.3 | 42.9 | 35.6 | 27.3 | 34.6 | 2 |
| Norit E Supra -peat | 29.7 | 20.0 | 34.2 | 23.4 | 3.4 | 14.2 | 2 |
| PAC 2000-900 -bituminous coal | 20.3 | 25.6 | 35.2 | 22.0 | −3.6 | 9.6 | 2 |
| Calgon C -bituminous coal | 13.9 | 7.4 | 25.2 | 22.0 | 14.6 | 17.8 | 1 |
| Darco KB -wood | 10.9 | 8.3 | 0.00 | 7.6 | −0.7 | −8.3 | 3 |
| Calgon WPX -bituminous coal | 4.0 | 8.8 | 46.6 | 26.0 | 17.2 | 37.8 | 1 |
| Norit CA 1 -wood | 7.9 | 6.0 | 0.00 | 0.00 | −6.0 | −6.0 | 3 |
| Norit SX4 -peat | 18.3 | 8.3 | 10.4 | 2.2 | −6.1 | 2.1 | 3 |
| Aquapac 800 -bituminous coal | 10.3 | 26.5 | 25.2 | 17.7 | −8.8 | −1.3 | 2 |
| Calgon BL -bituminous coal | 23.8 | 10.6 | 26.6 | 18.3 | 7.7 | 16.0 | 2 |
| PAC 2000-600 -bituminous coal | 7.5 | 21.0 | 12.1 | 6.5 | −14.5 | −8.9 | 2 |
| Chemcarb C25 -wood | 2.8 | 14.2 | 1.3 | 3.0 | −11.2 | −12.9 | 3 |
| Norit CASPF -wood | 2.8 | 10.6 | 0.00 | — | −10.6 | −10.6 | 3 |
| Calgon WPH -bituminous coal | 11.7 | 8.8 | 18.7 | — | −8.8 | 9.9 | 2 |
| Calgon RC -bituminous coal | 7.9 | 14.4 | 40.1 | 20.7 | 6.3 | 25.7 | 2 |
| Calgon Colorsorb -wood | 15.4 | 13.4 | 11.2 | — | −13.4 | −2.2 | 3 |
| Darco S-51 -lignite coal | 12.1 | 13.9 | 0.00 | 7.9 | −6.0 | −13.9 | 3 |
| Norit PAC 200 -bituminous coal | 5.1 | 14.8 | 28.5 | 19.8 | 5.0 | 13.7 | 2 |
| Calgon WPL -bituminous coal | 4.2 | 8.3 | 32.8 | — | −8.3 | 24.5 | 2 |

Figure 3:
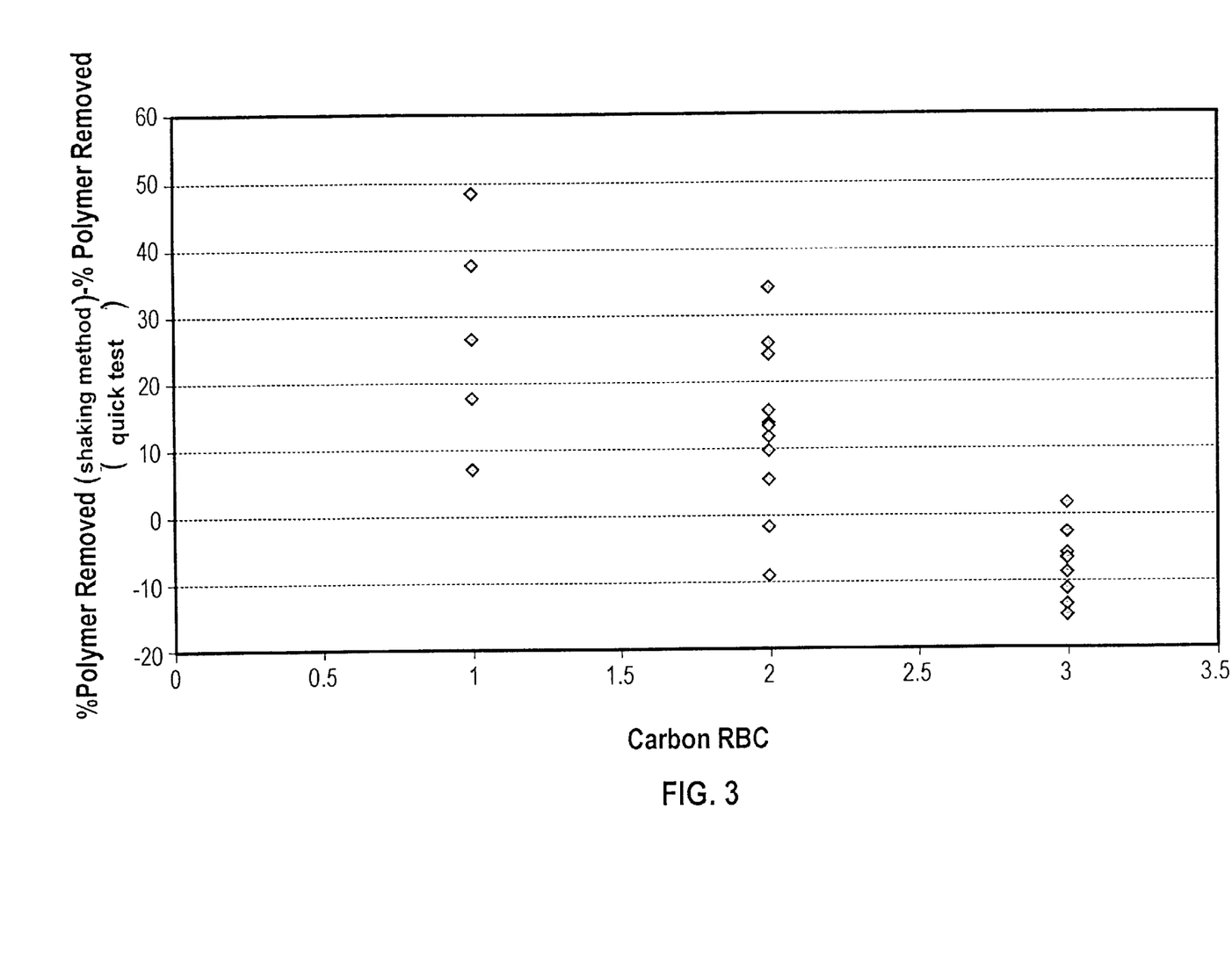
FIG. 3 depicts the difference in percentage of polymer removal between the "shaking method" and the "quick test" of candidate removal agents, described below.

Without limiting the invention to a particular mechanism of action, it is believed that carbonaceous materials of RBC 1 and RBC 2 had less available carbon surface area for polymer adsorption during the quick test than did carbonaceous materials having an RBC of 3. As shown in Table 1, the shaking method provided increased polymer adsorption capacity over either the quick test or the stirring method. The shaking method provided the following % polymer removal: for materials having an RBC of 1, as high as 53.9%; for materials having an RBC of 2, as high as 42.9%; and, for materials having an RBC of 3, as high as 22.4%. The stirring method provided the following % polymer removal: for materials having an RBC of 1, as high as 34.7%; for materials having an RBC of 2, as high as 35.6%; for materials having an RBC of 3, as high as 32.2%. Column "Delta" shows the difference in % removal between the stirring method and the quick test. Column "Max Delta" shows the difference in % removal between the shaking method and the quick test. Max Delta is plotted in FIG. 3 wherein a trend exists between the RBC and the difference in % removal between the shaking method and the quick test. As shown in FIG. 3, the difference in % removal was greatest for materials having an RBC of 1 and least for materials having an RBC of 3.

EXAMPLE 3

The procedures of Examples 1 and 2 are repeated using a jet fuel candidate, with the following results:

| Sample | % Polymer Removal Quick Test No Heat | % Polymer Removal Shaking Method | % Polymer Removal Stirring Method |
|---|---|---|---|
| Calgon RB | 59.1 | 14.7 | 54.5 |
| Calgon C | 43.1 | 14.7 | 42.2 |
| Calgon WPX | 64.5 | 19.4 | 63.3 |
| Calgon BL | 48.3 | 11.8 | 49.3 |
| Calgon WPH | 55.5 | 19.0 | 57.1 |
| Calgon RC | 33.2 | 12.8 | 45.5 |
| Calgon Colorsorb | 65.3 | 19.0 | 67.2 |

Based on the foregoing, a gradual or incremental add/stir procedure is more efficient in removing DRA from more viscous hydrocarbon fuels, such as jet fuel.

EXAMPLE 4

Activated carbon A is identified as an effective detection agent for DRA in gasoline, and is determined to have a DRA adsorption capacity of 0.2%. A canister or cartridge containing 10 pounds activated carbon A is incorporated in the fuel induction system of an automobile that is fueled by gasoline. The cartridge is positioned so that the gasoline passes through the cartridge after leaving the fuel tank and before entering the fuel injectors in a manner adapted to avoid impacting the overall performance-related fuel induction aspects of the vehicle. The gasoline used in the vehicle has a typical density of 5.38 pounds per gallon and a DRA polymer level of 10 ppm by weight. The cartridge removes the DRA from up to 372 gallons of the gasoline, which translates to 24 tank fulls of gasoline, assuming the vehicle has a fuel tank capacity of 15 gallons.

EXAMPLE 5

A fuel terminal comprises a DRA adsorption unit comprising a cylindrical vessel containing 10,000 pounds of an effective removal agent comprising activated carbon A. The vessel is constructed in an upflow design that allows liquid hydrocarbon fuel to enter at the bottom of the vessel and leave from the top. The DRA adsorption unit is located between the fuel storage tanks and the loading rack used by customers that purchase tanker truck quantities of fuel. The adsorption unit further comprises a bypass valve and loop that allows fuel to bypass the adsorption unit as it is pumped from a given terminal storage tank to the loading rack.

Each terminal tank of fuel is tested using activated carbon A as a detection agent. When the test indicates that DRA is present in a tank of liquid hydrocarbon fuel, the bypass valve to the adsorption unit is closed, thereby directing the liquid hydrocarbon fuel containing the DRA to pass from the tank and through the adsorption unit. When the test indicates that DRA is not present, the bypass valve is opened, thereby causing the fuel to bypass the adsorption unit as it is pumped from that terminal storage tank to the loading rack.

The 10,000 pound vessel of activated carbon removes the DRA from up to 372,000 gallons of the gasoline in the terminal tank.

Persons of ordinary skill in the art will recognize that many modifications may be made to the present invention without departing from the spirit and scope of the present invention. The embodiment described herein is meant to be illustrative only and should not be taken as limiting the invention.

We claim:

1. A method of selecting one or more removal agents effective to substantially reduce a concentration of drag reducer additive in a liquid hydrocarbon fuel, said method comprising:

providing motor gasoline comprising a quantity of a drag reducer additive;

forming a dispersion of a carbonaceous selection agent in said motor gasoline under conditions effective to agitate and observe said dispersion; and, selecting as said one or more removal agents said carbonaceous selection agents that produce visible agglomerates.

2. A method of selecting one or more removal agents effective to substantially reduce a concentration of drag reducer additive in a liquid hydrocarbon fuel, said method comprising:

providing an amount of motor gasoline comprising a quantity of a drag reducer additive;

forming a dispersion of a volume of activated carbon in said motor gasoline under conditions effective to agitate and observe said dispersion; and, selecting as said one or more removal agents said activated carbons that produce visible agglomerates.

3. The method of claim 2 wherein said selecting further comprises selecting said activated carbons that produce visible agglomerates that become glossy before or during their production.

4. The method of claim 2 wherein said conditions effective to agitate said dispersion comprise shaking said dispersion.

5. The method of claim 3 wherein said conditions effective to agitate said dispersion comprise shaking said dispersion.

6. The method of claim 5 wherein, when said volume of said one or more activated carbons is 0.5 gm, said amount of motor gasoline is 100 ml., and said quantity of drag reducer additive is 20 ppm, said one or more activated carbons reduce said 20 ppm of drag reducer additive by about 3% or more.

7. The method of claim 5 wherein, when said volume of said one or more activated carbons is 0.5 gm, said amount of motor gasoline is 100 ml., and said quantity of drag reducer additive is 20 ppm, said one or more activated carbons reduce said 20 ppm of drag reducer additive by about 20% or more.

8. The method of claim 5 wherein, when said volume of said one or more activated carbons is 0.5 gm, said amount of motor gasoline is 100 ml., and said quantity of drag reducer additive is 20 ppm, said one or more activated carbons reduce said 20 ppm of drag reducer additive by about 50% or more.

9. The method of claim 2 wherein said one or more activated carbons have a porosity sufficient to provide an adsorption capacity of about 0.05 wt. % or more.

10. The method of claim 2 wherein said one or more activated carbons have a porosity sufficient to provide an adsorption capacity of about 0.2 wt. % or more.

11. The method of claim 8 wherein said one or more activated carbons have a porosity sufficient to provide an adsorption capacity of about 0.05 wt. % or more.

12. The method of claim 8 wherein said one or more activated carbons have a porosity of sufficient to provide an adsorption capacity of about 0.2 wt. % or more.

13. A method of selecting one or more removal agents effective to substantially reduce a concentration of drag reducer additive in motor gasoline, said method comprising:
   providing motor gasoline comprising a quantity of a drag reducer additive;
   forming a dispersion of one or more carbonaceous selection agents in said motor gasoline under conditions effective to agitate and observe said dispersion; and,
   selecting as said one or more removal agents said one or more carbonaceous selection agents that produce visible agglomerates.

14. A method of selecting one or more removal agents effective to substantially reduce a concentration of drag reducer additive in motor gasoline, said method comprising:
   providing an amount of motor gasoline comprising a quantity of a drag reducer additive;
   forming a dispersion of a volume of one or more activated carbons in said motor gasoline under conditions effective to agitate and observe said dispersion; and,
   selecting as said one or more removal agents said one or more activated carbons that produce visible agglomerates.

15. The method of claim 14 wherein said selecting further comprises selecting said one or more activated carbons that produce visible agglomerates that become glossy before or during their production.

16. The method of claim 14 wherein said conditions effective to agitate said dispersion comprise shaking said dispersion.

17. The method of claim 15 wherein said conditions effective to agitate said dispersion comprise shaking said dispersion.

18. The method of claim 14 wherein, when said volume of said one or more activated carbons is 0.5 gm, said amount of motor gasoline is 100 ml., and said quantity of drag reducer additive is 20 ppm, said one or more activated carbons reduce said 20 ppm of drag reducer additive by about 3% or more.

19. The method of claim 14 wherein, when said volume of said one or more activated carbons is 0.5 gm, said amount of motor gasoline is 100 ml., and said quantity of drag reducer additive is 20 ppm, said one or more activated carbons reduce said 20 ppm of drag reducer additive by about 20% or more.

20. The method of claim 14 wherein, when said volume of said one or more activated carbons is 0.5 gm, said amount of motor gasoline is 100 ml., and said quantity of drag reducer additive is 20 ppm, said one or more activated carbons reduce said 20 ppm of drag reducer additive by about 50% or more.

21. The method of claim 14 wherein said one or more activated carbons have a porosity sufficient to provide an adsorption capacity of about 0.05 wt. % or more.

22. The method of claim 14 wherein said one or more activated carbons have a porosity sufficient to provide an adsorption capacity of about 0.2 wt. % or more.

23. The method of claim 20 wherein said one or more activated carbons have a porosity sufficient to provide an adsorption capacity of about 0.05 wt. % or more.

24. The method of claim 20 wherein said one or more activated carbons have a porosity sufficient to provide an adsorption capacity of about 0.2 wt. % or more.

25. A method of selecting one or more removal agents effective to substantially reduce a concentration of drag reducer additive in a liquid hydrocarbon fuel, said method comprising:
   providing said liquid hydrocarbon fuel comprising a quantity of a drag reducer additive;
   forming a dispersion of one or more carbonaceous selection agents in said liquid hydrocarbon fuel under conditions effective to agitate and observe said dispersion; and,
   selecting as said one or more removal agents said one or more carbonaceous selection agents that produce visible agglomerates.

26. The method of claim 25 wherein said one or more carbonaceous selection agents comprise one or more activated carbons.

27. A method of selecting one or more removal agents effective to substantially reduce a concentration of a given drag reducer additive in a liquid hydrocarbon fuel, said method comprising:
   providing motor gasoline comprising a quantity of said given drag reducer additive;
   forming a dispersion of one or more carbonaceous selection agents in said motor gasoline under conditions effective to agitate and observe said dispersion; and,
   selecting as said one or more removal agents said one or more carbonaceous selection agents having a rheological behavior category (RBC) selected from the group consisting of an RBC of 1, an RBC of 2, and an RBC of 3.

28. The method of claim 27 wherein said conditions effective to agitate said dispersion comprise a method of agitation selected from the group consisting of shaking said dispersion and stirring said dispersion.

29. A method of selecting one or more removal agents effective to substantially reduce a concentration of a given drag reducer additive in a liquid hydrocarbon fuel, said method comprising:
   providing motor gasoline comprising a quantity of said given drag reducer additive;
   forming a dispersion of one or more carbonaceous selection agents in said motor gasoline under conditions effective to agitate and observe said dispersion; and,
   selecting as said one or more removal agents said one or more carbonaceous selection agents having a RBC selected from the group consisting of an RBC of 1 and an RBC of 2.

30. The method of claim 29 wherein said conditions effective to agitate said dispersion comprise a method of agitation selected from the group consisting of shaking said dispersion and stirring said dispersion.

31. A method of selecting one or more removal agents effective to substantially reduce a concentration of a given drag reducer additive in a liquid hydrocarbon fuel, said method comprising:
   providing motor gasoline comprising a quantity of said given drag reducer additive;
   forming a dispersion of one or more carbonaceous selection agents in said motor gasoline under conditions effective to agitate and observe said dispersion; and,
   selecting as said one or more removal agents said one or more carbonaceous selection agents having a RBC of 1.

32. The method of claim 31 wherein said conditions effective to agitate said dispersion comprise shaking said dispersion.

33. A method of selecting one or more removal agents effective to substantially reduce a concentration of a given drag reducer additive in a liquid hydrocarbon fuel, said method comprising:

providing motor gasoline comprising a quantity of said given drag reducer additive;

forming a dispersion of one or more activated carbons in said motor gasoline under conditions effective to agitate and observe said dispersion; and, selecting as said one or more removal agents said one or more activated carbons having a RBC selected from the group consisting of an RBC of 1, an RBC of 2, and an RBC of 3.

34. The method of claim 33 wherein said conditions effective to agitate said dispersion comprise shaking said dispersion.

35. A method of selecting one or more removal agents effective to substantially reduce a concentration of a given drag reducer additive in a liquid hydrocarbon fuel, said method comprising:

providing motor gasoline comprising a quantity of said given drag reducer additive;

forming a dispersion of one or more activated carbons in said motor gasoline under conditions effective to agitate and observe said dispersion; and, selecting as said one or more removal agents said one or more activated carbons having a RBC selected from the group consisting of an RBC of 1 and an RBC of 2.

36. The method of claim 35 wherein said conditions effective to agitate said dispersion comprise shaking said dispersion.

37. A method of selecting one or more removal agents effective to substantially reduce a concentration of a given drag reducer additive in a liquid hydrocarbon fuel, said method comprising:

providing motor gasoline comprising a quantity of said given drag reducer additive;

forming a dispersion of one or more activated carbons in said motor gasoline under conditions effective to agitate and observe said dispersion; and, selecting as said one or more removal agents said one or more activated carbons having a RBC of 1.

38. The method of claim 37 wherein said conditions effective to agitate said dispersion comprise shaking said dispersion.

39. A method of detecting the presence of drag reducer additive in a liquid hydrocarbon fuel, said method comprising:

providing a sample of said liquid hydrocarbon fuel;

forming a dispersion of one or more effective removal agents in said sample under conditions effective to agitate and observe said dispersion; and, determining whether said dispersion produces visible agglomerates, thereby indicating the presence of drag reducer additive.

40. The method of claim 39 wherein said one or more effective removal agents are one or more activated carbons.

41. The method of claim 40 wherein said determining further comprises determining whether said dispersion produces visible agglomerates that become glossy before or during their production.

42. The method of claim 41 wherein said liquid hydrocarbon fuel is motor gasoline.

43. The method of claim 42 wherein said conditions effective to agitate said dispersion comprise shaking said dispersion.

44. The method of claim 41 wherein said liquid hydrocarbon fuel is jet fuel.

45. The method of claim 44 wherein said conditions effective to agitate said dispersion comprise stirring said dispersion.

46. The method of claim 40 wherein said one or more activated carbons have a porosity sufficient to provide an adsorption capacity of about 0.05 wt. % or more.

47. The method of claim 40 wherein said one or more activated carbons have a porosity sufficient to provide an adsorption capacity of about 0.2 wt. % or more.

48. The method of claim 41 wherein said one or more activated carbons have a porosity sufficient to provide an adsorption capacity of about 0.05 wt. % or more.

49. The method of claim 41 wherein said one or more activated carbons have a porosity sufficient to provide an adsorption capacity of about 0.2 wt. % or more.

50. A method of removing drag reducer additive from a liquid hydrocarbon fuel, said method comprising:

providing a contaminated liquid hydrocarbon fuel comprising a concentration of a drag reducer additive;

contacting said contaminated liquid hydrocarbon fuel with a quantity of one or more effective removal agents under conditions effective to substantially reduce said concentration of drag reducer additive, thereby producing a clean liquid hydrocarbon fuel.

51. The method of claim 50 wherein said conditions comprise adding said quantity of said one or more effective removal agents to said contaminated liquid hydrocarbon fuel in increments with agitation.

52. The method of claim 50 wherein said one or more effective removal agents have a porosity sufficient to provide an adsorption capacity of about 0.05 wt. % or more.

53. The method of claim 50 wherein said one or more effective removal agents have a porosity sufficient to provide an adsorption capacity of about 0.2 wt. % or more.

54. The method of claim 51 wherein said one or more effective removal agents have a porosity sufficient to provide an adsorption capacity of about 0.05 wt. % or more.

55. The method of claim 51 wherein said one or more effective removal agents have a porosity sufficient to provide an adsorption capacity of about 0.2 wt. % or more.

56. A method of removing drag reducer additive from a liquid hydrocarbon fuel, said method comprising:

providing a contaminated liquid hydrocarbon fuel comprising a concentration of a drag reducer additive;

contacting said liquid hydrocarbon fuel with a quantity of one or more effective carbonaceous removal agents under conditions effective to remove said drag reducer additive, thereby producing a clean liquid hydrocarbon fuel.

57. The method of claim 56 wherein said conditions comprise adding said quantity of said one or more effective carbonaceous removal agents to said contaminated liquid hydrocarbon fuel in increments with agitation.

58. The method of claim 56 wherein said one or more effective carbonaceous removal agents have a porosity sufficient to provide an adsorption capacity of about 0.05 wt. % or more.

59. The method of claim 56 wherein said one or more effective carbonaceous removal agents have a porosity sufficient to provide an adsorption capacity of about 0.2 wt. % or more.

60. The method of claim 57 wherein said one or more effective carbonaceous removal agents have a porosity sufficient to provide an adsorption capacity of about 0.05 wt. % or more.

61. The method of claim 57 wherein said one or more effective carbonaceous removal agents have a porosity sufficient to provide an adsorption capacity of about 0.2 wt. % or more.

62. A method of removing drag reducer additive from a liquid hydrocarbon fuel, said method comprising:

providing a contaminated liquid hydrocarbon fuel comprising a concentration of at least one drag reducer additive;

contacting said contaminated liquid hydrocarbon fuel with a quantity of one or more activated carbons comprising effective removal agents under conditions effective to substantially reduce said concentration of said at least one drag reducer additive, thereby producing a clean liquid hydrocarbon fuel.

63. The method of claim 62 wherein said conditions comprise adding said quantity of said one or more activated carbons to said contaminated liquid hydrocarbon fuel in increments with agitation.

64. The method of claim 62 wherein, when 0.5 gm of said one or more activated carbons is added to 100 ml. of motor gasoline comprising 20 ppm of a drag reducer additive with incremental addition and shaking, said one or more activated carbons reduce said 20 ppm of drag reducer additive by about 3% or more.

65. The method of claim 62 wherein, when 0.5 gm of said one or more activated carbons is added to 100 ml. of motor gasoline comprising 20 ppm of a drag reducer additive with incremental addition and shaking, said one or more activated carbons reduce said 20 ppm of drag reducer additive by about 20% or more.

66. The method of claim 62 wherein, when 0.5 gm of said one or more activated carbons is added to 100 ml. of motor gasoline comprising 20 ppm of a drag reducer additive with incremental addition and shaking, said one or more activated carbons reduce said 20 ppm of drag reducer additive by about 50% or more.

67. The method of claim 62 wherein said one or more activated carbons have a porosity sufficient to provide an adsorption capacity of about 0.05 wt. % or more.

68. The method of claim 62 wherein said one or more activated carbons have a porosity sufficient to provide an adsorption capacity of about 0.2 wt. % or more.

69. The method of claim 66 wherein said one or more activated carbons have a porosity sufficient to provide an adsorption capacity of about 0.05 wt. % or more.

70. The method of claim 66 wherein said one or more activated carbons have a porosity sufficient to provide an adsorption capacity of about 0.2 wt. % or more.

71. A method of removing drag reducer additive from motor gasoline, said method comprising:

providing a contaminated motor gasoline comprising a concentration of at least one drag reducer additive;

contacting said contaminated motor gasoline with a quantity of one or more effective removal agents under conditions effective to substantially reduce said concentration of said at least one drag reducer additive, thereby producing a clean motor gasoline.

72. A method of removing drag reducer additive from motor gasoline, said method comprising:

providing a contaminated motor gasoline comprising a concentration of at least one drag reducer additive;

contacting said contaminated motor gasoline with a quantity of one or more carbonaceous materials comprising effective removal agents under conditions effective to substantially reduce said concentration of said at least one drag reducer additive, thereby producing a clean motor gasoline.

73. The method of claim 72 wherein said conditions comprise adding said quantity of said one or more carbonaceous materials to said contaminated liquid hydrocarbon fuel in increments with agitation.

74. The method of claim 72 wherein said one or more carbonaceous materials have a porosity sufficient to provide an adsorption capacity of about 0.05 wt. % or more.

75. The method of claim 72 wherein said one or more carbonaceous materials have a porosity sufficient to provide an adsorption capacity of about 0.2 wt. % or more.

76. The method of claim 73 wherein said one or more carbonaceous materials have a porosity sufficient to provide an adsorption capacity of about 0.05 wt. % or more.

77. The method of claim 73 wherein said one or more carbonaceous materials have a porosity sufficient to provide an adsorption capacity of about 0.2 wt. % or more.

78. A method of removing drag reducer additive from motor gasoline, said method comprising:

providing a contaminated motor gasoline comprising a concentration of at least one drag reducer additive;

contacting said contaminated motor gasoline with a quantity of one or more activated carbons comprising effective removal agents under conditions effective to substantially reduce said concentration of said at least one drag reducer additive, thereby producing a clean motor gasoline.

79. The method of claim 78 wherein said conditions comprise adding said quantity of said one or more activated carbons to said contaminated liquid hydrocarbon fuel in increments with agitation.

80. The method of claim 79 wherein said agitation comprises shaking.

81. The method of claim 78 wherein, when 0.5 gm of said one or more activated carbons is added to 100 ml. of motor gasoline comprising 20 ppm of a drag reducer additive with incremental addition and shaking, said one or more activated carbons reduce said 20 ppm of drag reducer additive by about 3% or more.

82. The method of claim 78 wherein, when 0.5 gm of said one or more activated carbons is added to 100 ml. of motor gasoline comprising 20 ppm of a drag reducer additive with incremental addition and shaking, said one or more activated carbons reduce said 20 ppm of drag reducer additive by about 20% or more.

83. The method of claim 78 wherein, when 0.5 gm of said one or more activated carbons is added to 100 ml. of motor gasoline comprising 20 ppm of a drag reducer additive with incremental addition and shaking, said one or more activated carbons reduce said 20 ppm of drag reducer additive by about 50% or more.

84. The method of claim 78 wherein said one or more activated carbons have a porosity sufficient to provide an adsorption capacity of about 0.05 wt. % or more.

85. The method of claim 78 wherein said one or more activated carbons have a porosity sufficient to provide an adsorption capacity of about 0.2 wt. % or more.

86. A method of removing drag reducer additive from jet fuel, said method comprising:

providing a contaminated jet fuel comprising a concentration of at least one drag reducer additive;

contacting said contaminated jet fuel with a quantity of one or more effective removal agents under conditions effective to substantially reduce said concentration of said at least one drag reducer additive, thereby producing a clean jet fuel.

87. A method of removing drag reducer additive from jet fuel, said method comprising:

providing a contaminated jet fuel comprising a concentration of at least one drag reducer additive;

contacting said contaminated jet fuel with a quantity of one or more carbonaceous materials comprising effective removal agents under conditions effective to substantially reduce said concentration of said at least one drag reducer additive, thereby producing a clean jet fuel.

88. The method of claim 87 wherein said conditions comprise adding said quantity of said one or more carbonaceous materials to said contaminated liquid hydrocarbon fuel in increments with agitation.

89. The method of claim 88 wherein said agitation comprises stirring.

90. The method of claim 87 wherein said one or more carbonaceous materials have a porosity sufficient to provide an adsorption capacity of about 0.05 wt. % or more.

91. The method of claim 87 wherein said one or more carbonaceous materials have a porosity sufficient to provide an adsorption capacity of about 0.2 wt. % or more.

92. The method of claim 89 wherein said one or more carbonaceous materials have a porosity sufficient to provide an adsorption capacity of about 0.05 wt. % or more.

93. The method of claim 89 wherein said one or more carbonaceous materials have a porosity sufficient to provide an adsorption capacity of about 0.2 wt. % or more.

94. A method of removing drag reducer additive from jet fuel, said method comprising:
providing a contaminated jet fuel comprising a concentration of at least one drag reducer additive;
contacting said contaminated jet fuel with a quantity of one or more activated carbons comprising effective removal agents under conditions effective to substantially reduce said concentration of said at least one drag reducer additive, thereby producing a clean jet fuel.

95. The method of claim 94 wherein said conditions comprise adding said quantity of said one or more activated carbons to said contaminated jet fuel in increments with agitation.

96. The method of claim 95 wherein said agitation comprises stirring.

97. The method of claim 94 wherein, when 0.5 gm of said one or more activated carbons is added to 100 ml. of motor gasoline comprising 20 ppm of a drag reducer additive with incremental addition and shaking, said one or more activated carbons reduce said 20 ppm of drag reducer additive by about 3% or more.

98. The method of claim 94 wherein, when 0.5 gm of said one or more activated carbons is added to 100 ml. of motor gasoline comprising 20 ppm of a drag reducer additive with incremental addition and shaking, said one or more activated carbons reduces said 20 ppm of drag reducer additive by about 20% or more.

99. The method of claim 94 wherein, when 0.5 gm of said one or more activated carbons is added to 100 ml. of motor gasoline comprising 20 ppm of a drag reducer additive with incremental addition and shaking, said one or more activated carbons reduce said 20 ppm of drag reducer additive by about 50% or more.

100. The method of claim 94 wherein said one or more activated carbons have a porosity sufficient to provide an adsorption capacity of about 0.05 wt. % or more.

101. The method of claim 94 wherein said one or more activated carbons have a porosity sufficient to provide an adsorption capacity of about 0.2 wt. % or more.

102. The method of claim 96 wherein said one or more activated carbons have a porosity sufficient to provide an adsorption capacity of about 0.05 wt. % or more.

103. The method of claim 96 wherein said one or more activated carbons have a porosity sufficient to provide an adsorption capacity of about 0.2 wt. % or more.

* * * * *